(12) United States Patent
Duncan

(10) Patent No.: US 8,672,891 B1
(45) Date of Patent: Mar. 18, 2014

(54) IV LINE CLASP

(71) Applicant: Jessica L. Duncan, Colcord, OK (US)

(72) Inventor: Jessica L. Duncan, Colcord, OK (US)

(73) Assignee: Trenclasp LLC, Tulsa, OK (US)

( * ) Notice: Subject to any disclaimer, the term of this patent is extended or adjusted under 35 U.S.C. 154(b) by 0 days.

(21) Appl. No.: 13/803,529

(22) Filed: Mar. 14, 2013

(51) Int. Cl.
*A61M 5/32* (2006.01)

(52) U.S. Cl.
USPC .......................................................... 604/179

(58) Field of Classification Search
USPC ................................................ 604/177–180
See application file for complete search history.

(56) References Cited

U.S. PATENT DOCUMENTS

| | | | | |
|---|---|---|---|---|
| 2,409,432 A | * | 10/1946 | Hubbard | 604/179 |
| 2,449,882 A | * | 9/1948 | Daniels | 604/179 |
| 3,160,158 A | * | 12/1964 | Rayhart | 604/179 |
| 3,167,072 A | * | 1/1965 | Stone et al. | 604/179 |
| 3,782,378 A | * | 1/1974 | Page | 128/888 |
| 4,316,461 A | * | 2/1982 | Marais et al. | 604/179 |
| 4,326,517 A | * | 4/1982 | Whitney et al. | 604/155 |
| 4,453,933 A | * | 6/1984 | Speaker | 604/179 |
| 4,470,410 A | * | 9/1984 | Elliott | 128/877 |
| 4,591,356 A | | 5/1986 | Christie | |
| D290,041 S | * | 5/1987 | Scott | D24/128 |
| 4,919,150 A | | 4/1990 | Grant | |
| 5,084,026 A | * | 1/1992 | Shapiro | 604/179 |
| 5,131,412 A | | 7/1992 | Rankin | |
| 5,190,530 A | | 3/1993 | Greeff et al. | |
| 5,279,574 A | | 1/1994 | Forren | |
| 5,344,406 A | | 9/1994 | Spooner | |
| 6,000,402 A | | 12/1999 | Able | |
| 6,074,368 A | * | 6/2000 | Wright | 604/179 |
| 6,086,564 A | * | 7/2000 | McLaughlin | 604/179 |
| 6,500,154 B1 | * | 12/2002 | Hakky et al. | 604/174 |
| 6,526,981 B1 | * | 3/2003 | Rozier et al. | 128/846 |
| 7,198,616 B2 | * | 4/2007 | Mossanen-Shams et al. | 604/174 |
| 7,626,070 B2 | * | 12/2009 | Propp | 602/41 |
| 8,109,912 B2 | * | 2/2012 | Alferness et al. | 604/181 |
| 8,197,447 B2 | * | 6/2012 | Wright | 604/174 |
| 8,211,064 B2 | * | 7/2012 | Sloan | 604/179 |
| 8,298,191 B2 | * | 10/2012 | Bierman et al. | 604/180 |
| 8,500,698 B2 | * | 8/2013 | Kyvik et al. | 604/174 |
| 2004/0034330 A1 | * | 2/2004 | Bierman et al. | 604/500 |
| 2005/0131353 A1 | * | 6/2005 | Mossanen-Shams et al. | 604/179 |
| 2005/0137496 A1 | * | 6/2005 | Walsh et al. | 600/561 |
| 2009/0137962 A1 | * | 5/2009 | Bracken et al. | 604/179 |
| 2010/0106095 A1 | * | 4/2010 | Vitaris et al. | 604/177 |
| 2010/0114034 A1 | * | 5/2010 | Wright et al. | 604/177 |
| 2010/0179481 A1 | * | 7/2010 | Bierman et al. | 604/177 |
| 2010/0234804 A1 | * | 9/2010 | Hiejima et al. | 604/110 |

* cited by examiner

*Primary Examiner* — Nicholas Lucchesi
*Assistant Examiner* — Diva K Chander
(74) *Attorney, Agent, or Firm* — Molly D. McKay

(57) ABSTRACT

The present invention is an IV line clasp that has a contoured recessed channel provided in a head that is designed to receive and hold the IV equipment securely and has adjustable cotton straps attached on either side of the head that secure together on their ends via hook and loop fasteners to hold the IV in place on the patient's body without the use of tape.

7 Claims, 5 Drawing Sheets

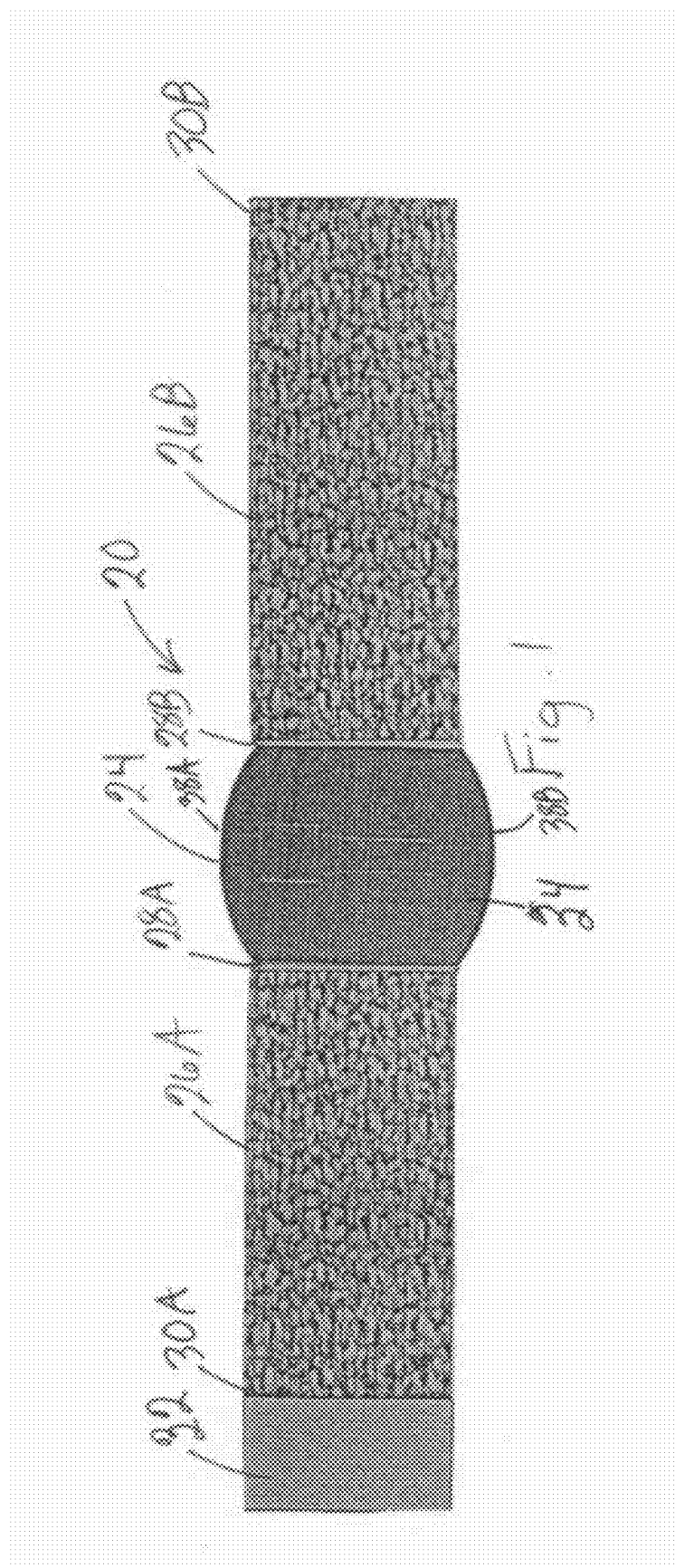

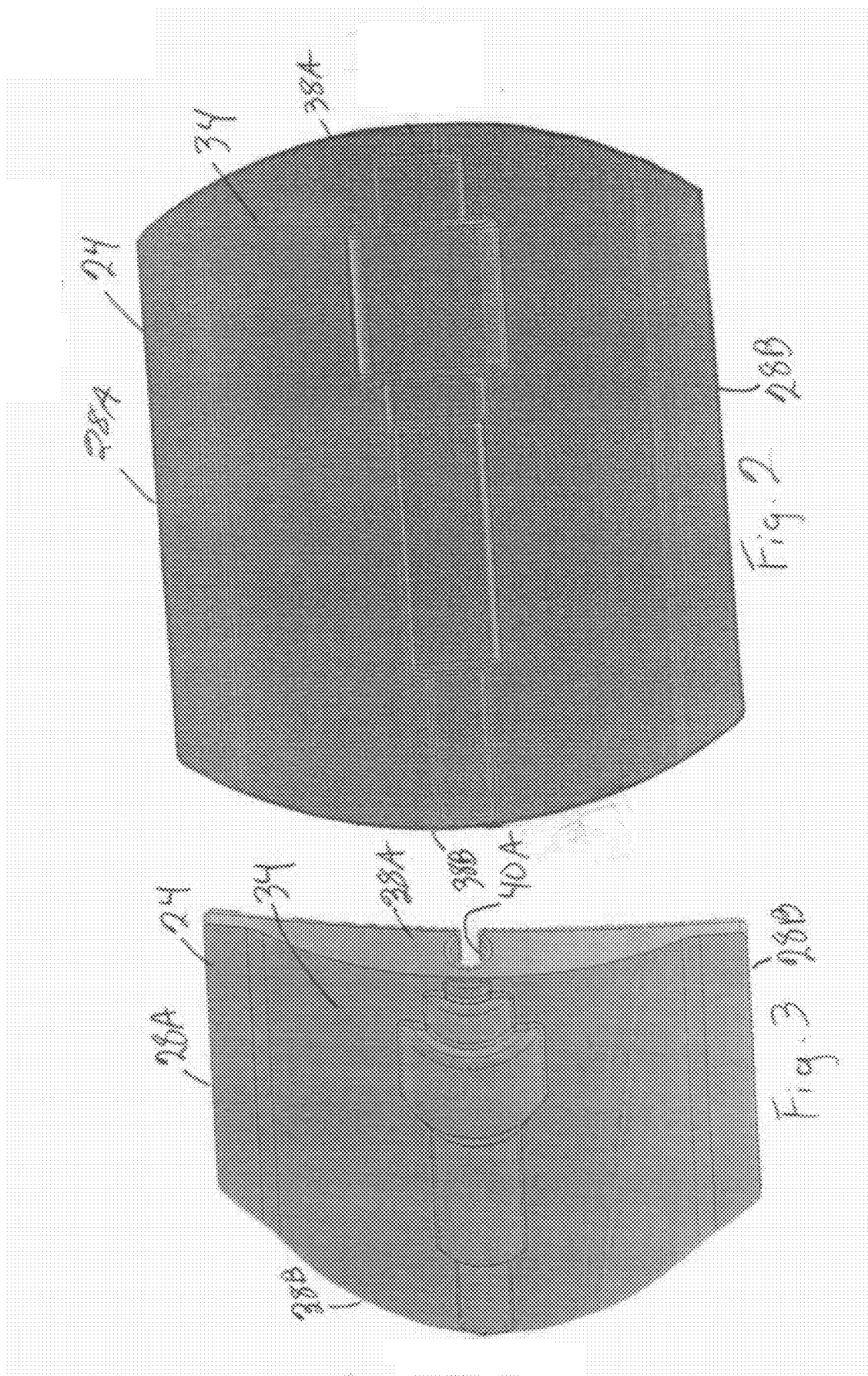

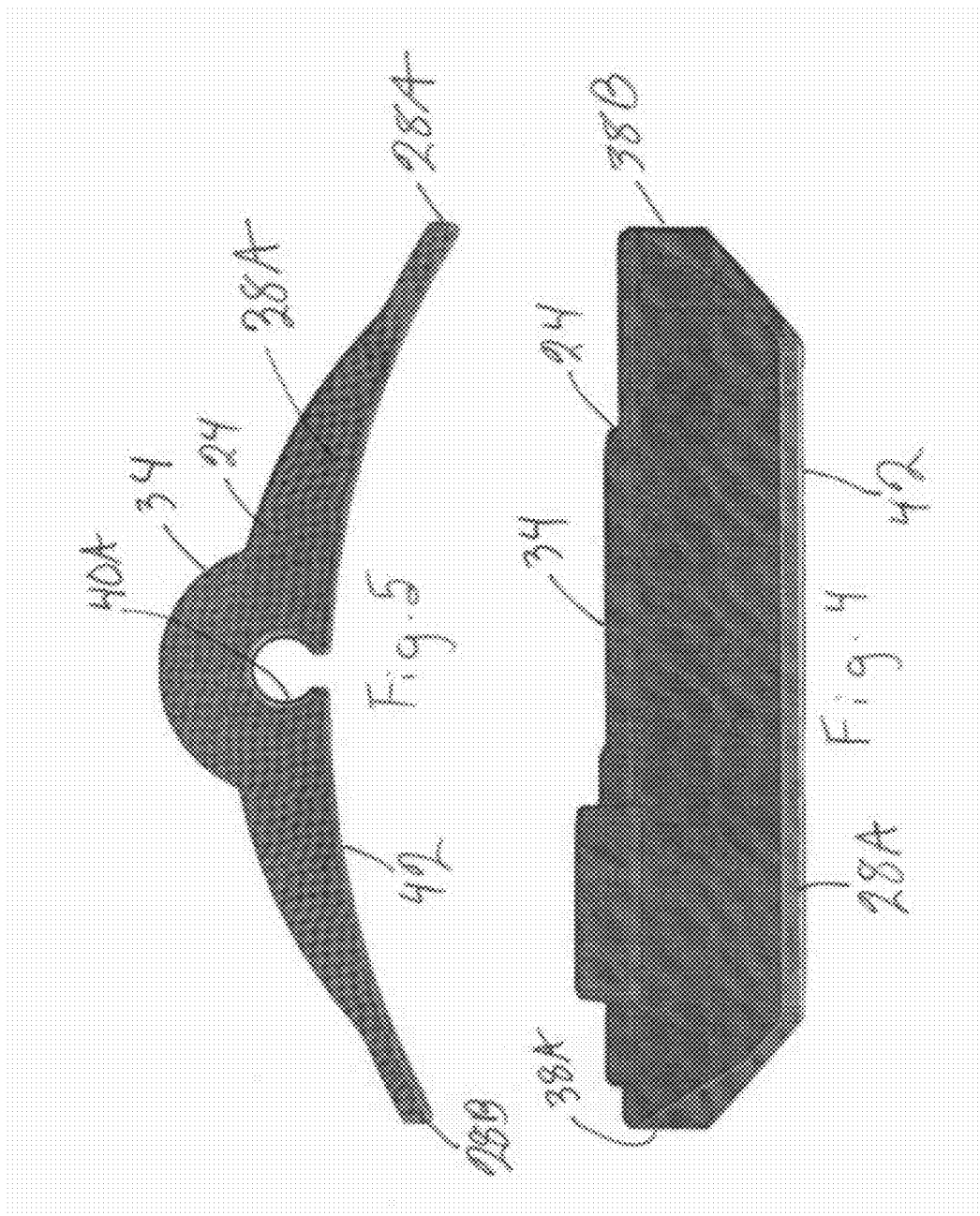

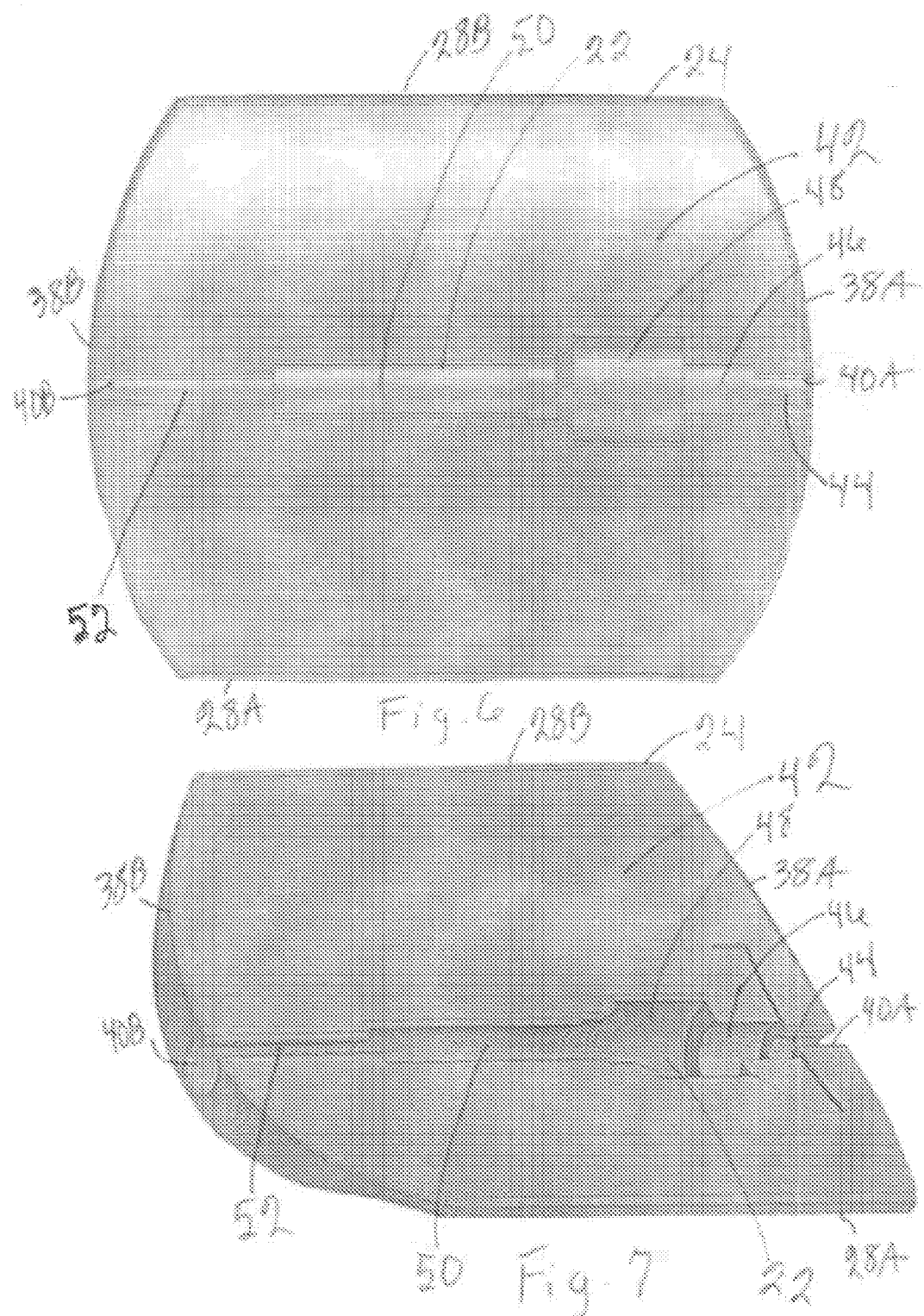

IV LINE CLASP

BACKGROUND OF THE INVENTION

1. Field of the Invention

The present invention relates to a device for holding a non-ported IV that is installed in a patient's body so that it does not move. Specifically, the invention is an IV line clasp that takes the place of tape to hold an IV line in place on the patient.

2. Description of the Related Art

The present method for holding an installed intravenous (IV) needle is to put tape or some type of elastic band around the IV and the patient's body where the IV is installed. The problem with using tape is that the IV can shift under the tape and become dislodged. A still further problem with use of tape is that the tape can cause allergic reactions, can irritate or actually cause the skin to be removed when the tape is removed from the patient's body. This is particularly problematic when the skin is delicate, such as on an infant or elderly person or where there has been damage to the skin, such as in the case of a burn patient.

Use of an elastic band around the patient's body to secure the IV is also problematic since the elastic band can cut off circulation and result in tissue damage or death of tissue, even to the point of the patient losing a limb.

The present invention addresses these problems by providing an IV line clasp that receives and holds the IV equipment securely within a contoured recess or channel provided in the head of the clasp and that has adjustable straps attached to the head that secure together to hold the IV in place on the patient's body without the use of tape.

SUMMARY OF THE INVENTION

The present invention is an IV line clasp that receives and holds the IV equipment securely within a contoured recess or channel provided in the head of the clasp and that has adjustable cotton straps attached on either side of the head that secure together on their ends via fasteners to hold the IV in place on the patient's body without the use of tape.

BRIEF DESCRIPTION OF THE DRAWINGS

FIG. 1 is a top plan view of an IV line clasp constructed in accordance with a preferred embodiment of the present invention.

FIG. 2 is a top plan view of the head of the IV line clasp of FIG. 1, shown with the straps removed.

FIG. 3 is a top perspective view of the head of FIG. 2.

FIG. 4 is a side view of the head of FIG. 2.

FIG. 5 is an end view of the head of FIG. 2.

FIG. 6 is bottom plan view of the head of FIG. 2.

FIG. 7 is bottom perspective view of the head of FIG. 2.

DETAILED DESCRIPTION OF THE PREFERRED EMBODIMENT

Figure 8:
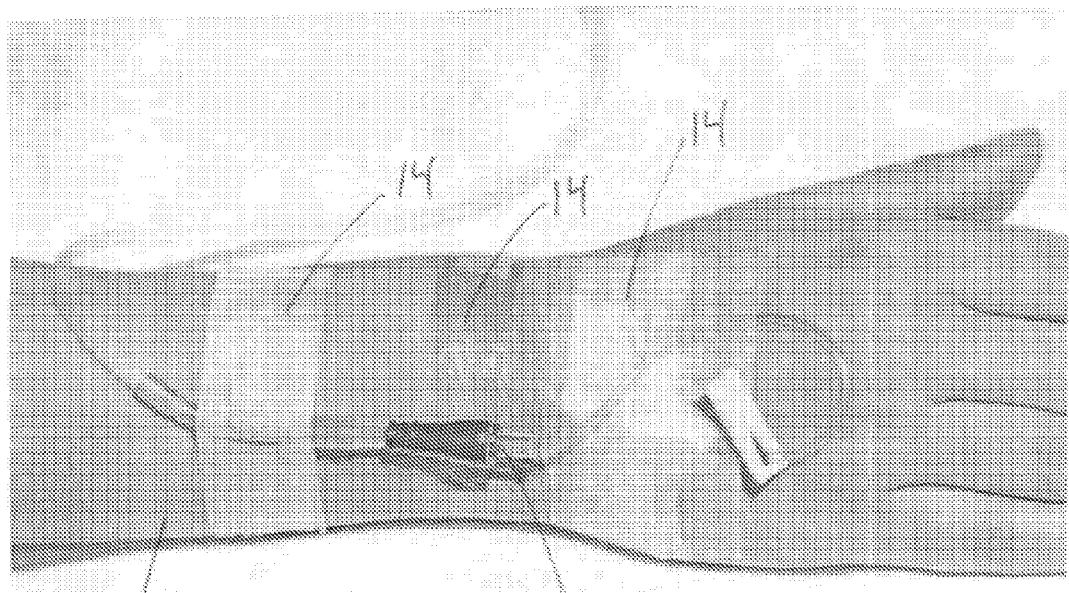
FIG. 8 is a perspective view of a prior art IV installation in the hand of a patient, showing the IV equipment secured to the patient's hand with tape.

Referring initially to FIG. 8, there is shown a typical prior art method of securing IV equipment 10 to a patient's body 12 with tape 14. It is important that the IV equipment 10 be secured to the patient's body 12 so that the IV catheter which is inserted into a vein in the patient's body 12 does not become dislodged which would require installation of a new IV catheter. However, use of tape 14 for this purpose is problematic.

Referring to FIG. 1, there is illustrated an IV line clasp 20 that is constructed in accordance with a preferred embodiment of the present invention.

The invention is an IV line clasp 20 that receives and holds the IV equipment 10 securely within a contoured recess or channel 22 provided in a centrally located head 24 of the clasp 20. The head 24 is preferably constructed of molded plastic. Adjustable cotton straps 26A and 26B are attached on opposite ends 28A and 28B of the head 24 that secure together on distal ends 30A and 30B of the straps 26A and 26B via fasteners 32 provided on the ends 30A and 30B to hold the IV equipment 10 in place on the patient's body 12 without the use of tape 14.

The straps 26A and 26B are adjustable in length and are designed to be secured together around the patient's body 12 with fasteners 32, such as the hook and loop fastener that is illustrated. The straps 26A and 26B are preferably constructed of a comfortable, non-allergenic material that has a minimal amount of stretching capacity, such as the cotton bands that are illustrated.

FIGS. 2-7 show the detail of the head 24. The top 34 of the head 24 is arched upward and is preferably provided with a smoothly curved and contoured shape so that it is not easily snagged. The ends 28A and 28B of the head 24 are straight and approximately parallel with each other, and the straps 26A and 26B attached to the head 24 at the ends 28A and 28B. Each of the two sides 38A and 38B the head 24 is provided with a circular opening 40A and 40B. The two circular openings 40A and 40B are connected together on the underside 42 of the head 24 to form the channel 22 in which the IV equipment 10 inserts when the clasp 20 is in use, as will be more fully described hereafter.

Referring to FIGS. 6 and 7, the channel 22 is shaped, sized, and contoured to receive therein the IV equipment 10. Specifically, the channel 22 is provided with an IV catheter receiving section 44 that connects with the first circular opening 40A. The IV catheter receiving section 44 connects to a butterfly receiving section 46, and the butterfly receiving section 46 connects to a hub receiving section 48. The hub receiving section 48 connects to a hep lock receiving section 50, and the hep lock receiving section 50 connects to an IV line receiving section 52. The IV line receiving section 52 connects with the second circular opening 40B.

In use, the IV catheter is first installed in the patient's body 12. Then the IV line clasp 20 is placed over the IV equipment 10 so that the IV catheter of the IV equipment 10 inserts into the IV catheter receiving section 44 of the channel 22, the butterfly wings of the IV equipment 10 inserts into the butterfly receiving section 46, the hub of the IV equipment 10 inserts into hub receiving section 48, the hep lock or heparin containing lock of the IV equipment 10 inserts into the hep lock receiving section 50, and the IV line of the IV equipment 10 inserts into the IV line receiving section 52. When the IV equipment 10 is thus inserted into the channel 22, the IV catheter will exit the head 24 via the first circular opening 40A and the IV line will exit the head 24 via the second circular opening 40B. After the IV equipment 10 has been thus received in the channel 22, the straps 26A and 26B are extended around the patient's body 12 and secured together via fasteners 32 in order to secure the IV equipment 10 to the patient's body 12. The straps 26A and 26B are then adjusted in length to have a secure, but not a tight fit around the patient's body 12 so that the patient's circulation is not affected.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. An IV line clasp for securing an IV to a patient's body without the use of tape comprising:
   a head provided with a channel for receiving IV equipment, said channel shaped and sized to receive IV equipment therein, said channel terminates in a first circular opening and a second circular opening provided on opposite sides of the head,
   two adjustable length straps provided on opposite ends of the head, and fastening means for securing distal ends of the straps to each other to secure the head to a patient's body,
   an IV catheter receiving section of the channel that connects to the first circular opening, the IV catheter receiving section connects to a butterfly receiving section of the channel, the butterfly receiving section connects to a hub receiving section of the channel, the hub receiving section connects to a hep lock receiving section of the channel, the hep lock receiving section connects to an IV line receiving section of the channel, and the IV line receiving section connects with the second circular opening.

2. An IV line clasp according to claim 1 wherein the first circular opening is sized to allow an IV catheter to enter the channel on one side of the head, and the second circular opening is sized to allow an IV line to enter the channel on an opposite side of the head.

3. An IV line clasp according to claim 1 wherein the fastening means is a hook and loop type fastener provided on the ends of the straps.

4. An IV line clasp according to claim 1 wherein the straps are cotton straps that have minimal amount of stretching capacity.

5. An IV line clasp according to claim 1 wherein a top of the head is smoothly curved and contoured so it is not easily snagged.

6. An IV line clasp according claim 1 wherein the channel is provided in the underside of the head.

7. An IV line clasp according to claim 1 wherein the head is constructed of plastic.

* * * * *